United States Patent [19]

Bolt

[11] 4,204,282

[45] May 27, 1980

[54] IMPLANTABLE ARTIFICIAL SPHINCTER

[76] Inventor: Richard A. Bolt, Suite 400 Medical Arts Bldg., 1012 Volusia Ave., Daytona Beach, Fla. 32015

[21] Appl. No.: 903,825

[22] Filed: May 8, 1978

[51] Int. Cl.² .......................... A61F 1/00; A61F 1/24
[52] U.S. Cl. ........................................... 3/1; 128/1 R; 128/DIG. 25; 128/283
[58] Field of Search ................ 3/1, 1.4; 128/283, 1 R, 128/DIG. 25

[56] References Cited

U.S. PATENT DOCUMENTS

| | | | |
|---|---|---|---|
| 3,216,420 | 11/1965 | Smith et al. | 128/283 |
| 3,646,616 | 3/1972 | Keshin | 3/1 |
| 3,974,533 | 8/1976 | Klecker | 128/283 |

FOREIGN PATENT DOCUMENTS 2558521  6/1977  Fed. Rep. of Germany ... 128/DIG. 25

OTHER PUBLICATIONS

"Vitallium Tubes in Biliary Surgery" by H.E. Pearse, Annals of Surgery, vol. 115, No. 6, Jun. 1942.

*Primary Examiner*—Ronald L. Frinks
*Attorney, Agent, or Firm*—Carothers and Carothers

[57] ABSTRACT

An implantable artificial sphincter in the form of a sleeve for receiving and supporting therein the remaining terminal end of healthy bowel tissue. The sleeve is provided with multiple openings therethrough for the growth and passage of anchoring fibrous granulation tissue and the sleeve is provided with a removable closure which is position in the patient at the point were the anal sphincter was surgically removed thereby providing an artificial sphincter in near normal anatomical position.

8 Claims, 3 Drawing Figures

U.S. Patent May 27, 1980 4,204,282
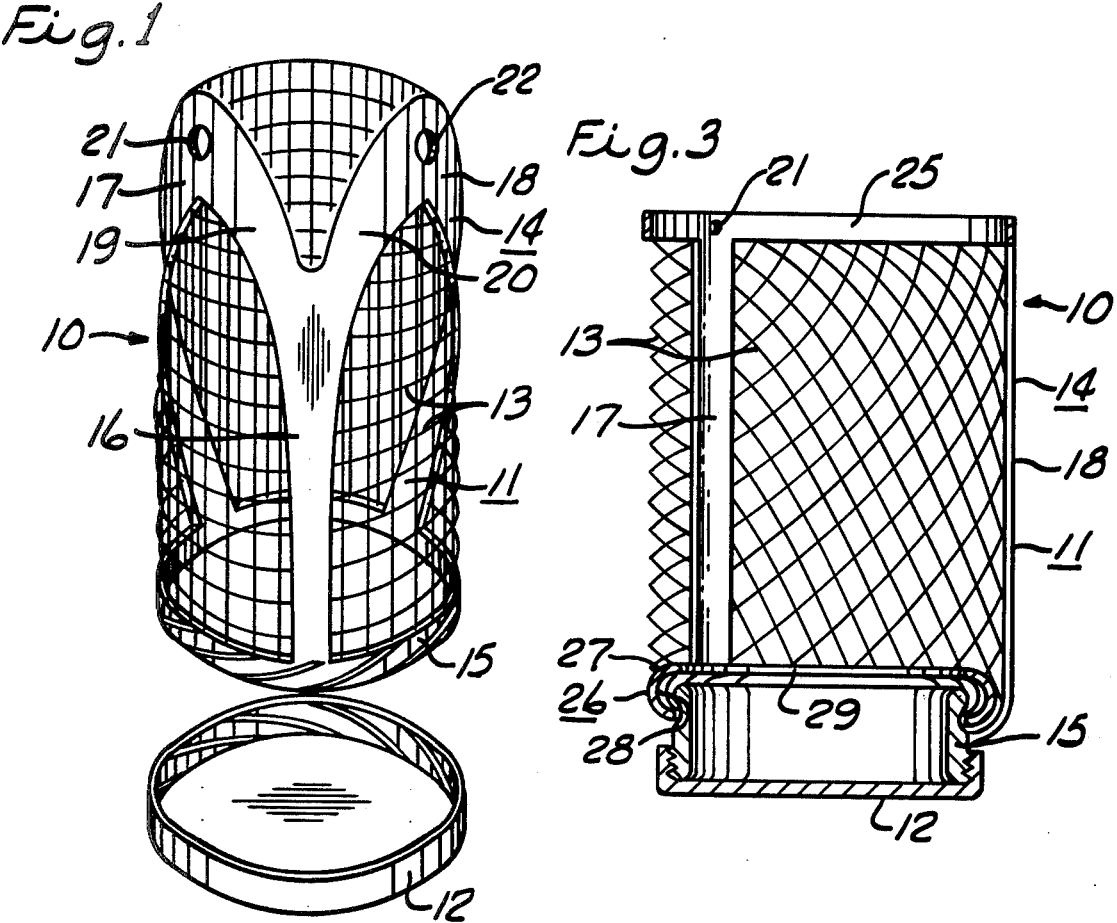
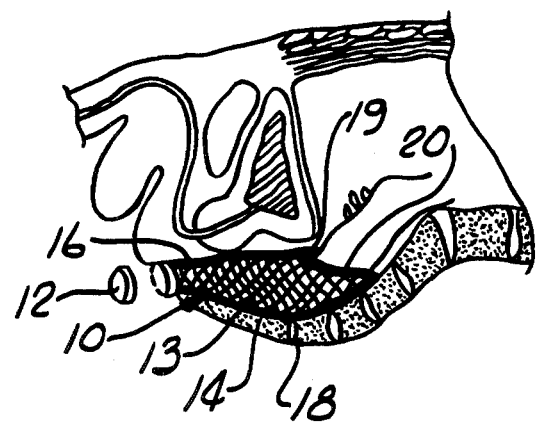

IMPLANTABLE ARTIFICIAL SPHINCTER

BACKGROUND OF THE INVENTION

This invention relates to a surgical appliance and more particularly to an implantable artificial sphincter which is permanently implanted within the patient after removal of the rectum in a nearly normal anatomical position eliminating the need for bulky external appliances and eliminating the worries of odor and soilage normally encountered in ileostomies or colostomies wherein an artificial rectal opening is constructed in the abdominal area of the patient.

Surgical removal of the rectum is currently utilized due to malignant or other infections of the colon or intestinal tract. The operation is generally referred to as an ileostomy or colostomy and a stoma or artificial rectal opening is constructed in the abdominal area of the patient and results in the necessity for providing some type of mechanism to catch and contain the flow of intestinal contents, which is usually continuous. In most cases, this is accomplished by everting a portion of remaining healthy bowel into an opening in the abdominal wall and arranging a tight-fitting seal around the stoma bud (everted bowel) so as to prohibit the deleterious effect of bowel contents on the surrounding skin. In addition, a removable container, usually in the shape of a pliable plastic bag, is attached to the seal around the stoma as an intermittently disposable reservoir.

There has been very little success in adapting this surgical procedure to use in the normal anatomical position between the gluteal crease, or at the position of the surgically removed sphincter because of the irregular shape of the tissue in this area, and also because of the demands of change in body position, such as sitting, etc., which act as a deterrent to accomplishing the adoption of a water-tight seal at the normal rectal area.

It is a principal object of the present invention to provide an implantable artificial sphincter which is anatomically positioned at a normal or near normal position in the rectal canal and which provides a leak-proof seal and dispenses with any requirement for external plastic bags or reservoirs or external appliances, thereby eliminating the worries of odor and soilage and the undesirable appearance of an artificial rectal opening in an unnatural position on the body.

SUMMARY OF THE INVENTION

Surgical removal of the rectum results in a potential cylindrical presacral space in which the artificial sphincter of the present invention is implanted together with the terminal end of the healthy remaining bowel. The implantable artificial sphincter of the present invention comprises a sleeve for supporting the terminal end of the healthy bowel therein. In other words, the terminal end of the remaining healthy bowel is telescoped within the sleeve and the sleeve is, in turn, secured in the aforesaid presacral space. The sleeve is provided with multiple openings therethrough for the subsequent growth and passage of anchoring fibrous granulation tissue which subsequently grows to anchor the bowel to the presacral space through the sleeve. One end of this sleeve is exposed at the anal or presacral space body opening and is provided with a removable closure. The artificial sphincter is constructed of synthetic material such as stainless steel or plastics that are strong and inert and readily absorbed into regenerating fibrous tissue that normally grows into the presacral space.

The healthy terminal segment of bowel is thus telescoped into the sleeve to a level distally equal to the point where the closure is secured and the bowel is secured to the sleeve, and the sleeve in turn is secured to the surrounding tissue of the presacral space. In time, anchoring fibrous granulation tissue grows through the fine interstices or openings in the sleeve, thereby solidly anchoring the terminal bowel portion to the sleeve and in turn, the sleeve to the presacral space, and thereby also forming a natural seal between the bowel, prosthesis and pelvic wall. Thus, the natural growth of the granulation tissue not only provides the necessary seal to the inner cavities of the body, but also solidly anchors the sleeve so that the sphincter closure exposed to the exterior of the body at the anal area may be manipulated as required to remove and purge the bowel and replace the cap without worry of disturbing the anchored sleeve. The sphincter closure may be in the form of a conventional screw-on cap or any other type of leak-proof plug arrangement.

The sleeve utilized in the artificial sphincter of the present invention may consist of a mesh sleeve such as a plastic or stainless steel mesh cylinder or sleeve having a more rigid sleeve support. The sleeve support may generally consist of a ring member for receiving the closure at the exposed end of the sleeve and a plurality of struts which extend from the ring member generally in the axial direction with the mesh sleeve secured to or integrally molded with these strut supports. As another alternative, the sleeve may be a perforated sleeve which is more rigid than ordinary screen or mesh, thereby eliminating the need for strut supports altogether.

If such strut supports are utilized, they are preferably equa-circumferentially spaced on the ring member. In addition, a second ring member may also be provided to secure the free ends of the struts together at the top of the sleeve.

In another embodiment, three struts may be provided, wherein one of the struts is bifurcated and the free ends of the bifurcation are secured respectively to the free ends of the remaining two struts in order to add strength to the strut support which depends from the ring member. If the closure to be utilized in the artificial sphincter of the present invention is in the form of a conventional screw-on cap, then the external exposed end of the ring member is conventionally threaded to receive a conventional screw-on cap.

In some instances, it may be desirable to evert the terminal end of the bowel at the rectal opening and create a stoma bud. In order to accomplish this, and to provide a better initial seal at the rectal opening, an additional clamp means is provided which will annularly secure the terminus of the bowel to the aforesaid ring member. This clamp means may consist of a snap ring member which cooperatively snaps to the inside end of the aforesaid ring member with sufficient tolerance between the ring member and the snap ring for the passage of the terminus end of the bowel which is being everted. This clamp means or ring may also be merely secured by other conventional means such as a suture to clamp the everted bowel terminus down onto the inside top end of the aforesaid ring member to which the closure is in turn secured.

The closure may also take on other forms besides a screw cap or plug, and may be in the form of a mechanical sphincter, say something similar to the shutter of a camera, which is operated mechanically or electrically. For example, a properly designed flexible type iris valve can be employed for the closure.

BRIEF DESCRIPTION OF THE DRAWINGS

Other objects and advantages appear in the following description and claims.

The accompanying drawings show, for the purpose of exemplification without limiting the invention or the claims thereto, certain practical embodiments illustrating the principles of this invention wherein:

FIG. 1 is an isometric view of one embodiment of the implantable artificial sphincter of the present invention.

FIG. 2 is a view in vertical cross section of the human body in sagital position illustrating the artificial sphincter of FIG. 1 implanted within the body.

FIG. 3 is a view in side elevation and in vertical section illustrating another embodiment of the implantable artificial sphincter of the present invention.

DETAILED DESCRIPTION OF THE DRAWINGS

Referring to FIG. 1, the implantable artificial sphincter 10 consists of a sleeve 11 for supporting the terminal end of a bowel therein and a removable closure 12 for closing one end of the sleeve 11. As can be seen in the Figure, sleeve 11 is provided with many openings or interstices therethrough for the passage of anchoring fibrous granulation tissue after the artificial sphincter has been implanted in the human body. In this particular embodiment, the multiple openings or interstices are provided by mesh sleeve 13 having a mesh sleeve support 14 in the form of a ring member 15 with three struts 16, 17 and 18, respectively, that extend upwardly from ring member 15 generally in the axial direction of sleeve 11. The mesh sleeve 13 may either be secured to the support member 14 or it may be integrally molded therewith.

Strut 16 is bifurcated at the upper end thereof thereby forming bifurcation struts 19 and 20. The outer ends of bifurcation struts 19 and 20 integrally mate or are formed with the outer ends of struts 17 and 18.

In this embodiment, the entire sleeve structure 11 is integrally molded of a suitable plastic, including the mesh sleeve 13 which is also molded integrally between the strut members of the support member 14. However, as previously indicated, mesh sleeve 13 may be secured to support member 14 independently and the mesh sleeve 13 may be formed of any suitable inert plastic or of a metal such as stainless steel which will not react with or be rejected by the human body.

The upper ends of struts 17 and 18 are provided with openings 21 and 22 respectively to assist in initially securing the apparatus to surrounding body tissue by the use of suture. The sleeve 11 may be secured by suture to the body cavity initially at a number of different locations to initially secure the device to the surrounding body tissue to provide sufficient anchorage until anchoring fibrous granulation tissue of the body has an opportunity to grow and naturally anchor the sleeve within the body cavity.

Ring member 15 is provided with conventional threads as indicated and closure 12 is threadably received on ring member 15 thereby providing an artificial sphincter closure which may be manually opened and closed by the patient to periodically evacuate the bowels.

When the rectum is removed from the patient by surgery, the perforated sleeve 11 is then inserted into the remaining anal body cavity opening and secured therein as illustrated in FIG. 2. The terminus of the remaining healthy bowel is then telescoped down into sleeve 11 all the way to the bottom of ring member 15. This portion of the bowel is anchored by suture or other suitable means to sleeve 11 as was sleeve 11 previously anchored to the surrounding body cavity. In time, anchoring fibrous granulation tissue will grow within the body cavity where sleeve 11 has been implanted, thereby anchoring the healthy bowel telescoped within sleeve 11 to the sleeve and to the body cavity. The sleeve 11 thus becomes firmly anchored within the body cavity, as does the bowel, and the growth of this granulation tissue also naturally seals off the abdominal cavity of the patient to the exterior, and thereby also prevents the possible seepage of bowel content into the abdominal cavity. As illustrated in FIG. 2, the sleeve 11 is implanted and is such that the ring member 15 is at the level of anal verge so that the closure 12 can be readily secured thereon and removed therefrom.

Any number of struts 16, 17 and 18 may be employed. In fact, the entire sleeve 11 may be manufactured as a cylinder with multiple perforations. The object is to provide a flexible sleeve member with multiple perforations and means to secure some type of closure to one end of the sleeve as an artificial sphincter closure. It should also be realized that any type of suitable closure may be employed and that the closure may be in the form of an iris valve or as an electrically operated shutter valve, or in the form of any conventional expansible plug, to name a few examples.

Referring next to FIG. 3, another embodiment of the artificial sphincter of the present invention is illustrated, and similar or identical parts are designated with the same reference numerals. The primary difference in this embodiment is that none of the struts is bifurcated, and all three struts are essentially straight and their upper free ends are joined unitarily by ring 25. In addition, a clamp means 26 is provided to annularly secure the terminus end of a tubular bowel telescoped within sleeve 11 to the ring member 15.

This clamp means consists of snap ring member 27, which is an annular ring member that cooperatively snaps to the inside or upper end of ring member 15 with sufficient tolerance 28 therebetween for the passage of the terminus end of a bowel. Thus, the terminus end of the bowel passes through opening 29 in ring member 27, and it is then also annularly passed through the tolerance or opening 28 and the ring member 27 is then snapped down over the upper end of ring member 15 to securely snap the bowel terminus annularly in the tolerance indicated by numeral 28. A small terminal portion of the bowel passing through tolerance 28 may be exposed to the outside of ring member 15 and then everted or annularly inverted and annularly sewn or sutured to the anal verge opening of the body cavity in a somewhat similar fashion as a stoma would be formed in a colostomy. This provides a better initial seal between the terminal end of the bowel and the surrounding body cavity.

I claim:

1. An implantable artificial sphincter comprising a sleeve for supporting the terminal end of a bowel therein, said sleeve having multiple openings therethrough for the passage of anchoring fibrous granulation tissue, one end of said sleeve provided with a removable closure, said sleeve consisting of a sleeve support including a ring member for receiving said closure at said one end and a plurality of struts extending from said ring member generally in the axial direction and a mesh sleeve secured to or integral with said support.

2. The artificial sphincter of claim 1 including three of said struts equa-circumferentially spaced on said ring member.

3. The artificial sphincter of claim 2 including a second ring member securing the free ends of said struts together.

4. The artificial sphincter of claim 2 wherein one of said struts is bifurcated and the free ends of the bifurcation curve and are secured to the free ends of the remaining two struts.

5. The artificial sphincter of claim 1 including clamp means to annularly secure the terminus of a bowel to said ring member.

6. The artificial sphincter of claim 5 wherein said clamp means consists of a snap ring member which cooperatively snaps to the inside end of said ring member with tolerance therebetween for the passage of the terminus end of a bowel.

7. The artificial sphincter of claim 1 wherein said closure is a cap threadably received on said one end of said sleeve.

8. The artificial sphincter of claim 1 including means to secure said sleeve to surrounding body tissue with suture.